US007490610B2

(12) United States Patent
Franklin

(10) Patent No.: US 7,490,610 B2
(45) Date of Patent: Feb. 17, 2009

(54) FALL PROTECTION HARNESS

(76) Inventor: Scott D. Franklin, 304 W. 6th St., Nederland, CO (US) 80466

( * ) Notice: Subject to any disclaimer, the term of this patent is extended or adjusted under 35 U.S.C. 154(b) by 642 days.

(21) Appl. No.: 10/793,170

(22) Filed: Mar. 4, 2004

(65) Prior Publication Data

US 2005/0121040 A1 Jun. 9, 2005

Related U.S. Application Data

(60) Provisional application No. 60/527,992, filed on Dec. 9, 2003.

(51) Int. Cl.

| | |
|---|---|
| ***A61F 5/37*** | (2006.01) |
| ***A61B 19/00*** | (2006.01) |
| ***A62B 35/00*** | (2006.01) |
| ***E06C 7/18*** | (2006.01) |

(52) U.S. Cl. .......................... 128/875; 128/869; 182/3; 182/6; 297/468

(58) Field of Classification Search ................. 128/869, 128/873, 875, 876; 482/105; 602/60-62, 602/78, 24; 182/3, 5-7; 297/468, 464, 488
See application file for complete search history.

(56) References Cited

U.S. PATENT DOCUMENTS

| | | | | |
|---|---|---|---|---|
| 908,533 | A * | 1/1909 | Zuckriegel | 602/61 |
| 937,724 | A * | 10/1909 | Small | 128/98.1 |
| 1,642,911 | A * | 9/1927 | Thurnau | 182/3 |
| 2,252,998 | A * | 8/1941 | Wachtel | 182/6 |
| 2,448,066 | A * | 8/1948 | Wilson | 244/151 R |
| 2,960,180 | A * | 11/1960 | Wachtel | 182/3 |
| 3,068,862 | A * | 12/1962 | Fuzere | 602/24 |
| 3,159,241 | A | 12/1964 | Martin | |
| 3,260,259 | A * | 7/1966 | Connelly | 602/24 |

(Continued)

FOREIGN PATENT DOCUMENTS

DE 2933771 A1 3/1981

(Continued)

OTHER PUBLICATIONS

British Standard BS EN 12277:1998 "Mountaineering equipment—Harnesses—Safety requirements and test methods" (1998).

(Continued)

*Primary Examiner*—Keri J Nicholson
(74) *Attorney, Agent, or Firm*—Hoffmann & Baron, LLP

(57) ABSTRACT

A fall protection harness that includes: an adjustable belt having a front, a back, a first side and a second side; a tie-in point; a first weight supporting loop having a first front section connected to the front of the belt and a first back section connected to the back of the belt; a second weight supporting loop having a second front section connected to the front of the belt and a second back section connected to the back of the belt; a first lateral member extending between the first front section and the first back section; and a second lateral member extending between the second front section and the second back section. The weight supporting loops and the lateral members define openings that are adapted to encircle a wearer's legs, and the back sections are adapted to support the wearer's lower back and/or buttocks.

8 Claims, 11 Drawing Sheets

U.S. PATENT DOCUMENTS

| | | | | | |
|---|---|---|---|---|---|
| 3,322,102 | A | * | 5/1967 | Windle | 182/3 |
| 3,415,340 | A | * | 12/1968 | Kinkade | 182/7 |
| 3,869,021 | A | * | 3/1975 | Sutherland et al. | 182/3 |
| 3,937,461 | A | * | 2/1976 | Lew | 482/43 |
| 4,132,055 | A | | 1/1979 | Bird | |
| 4,508,045 | A | * | 4/1985 | Spanier | 114/39.18 |
| 4,645,033 | A | | 2/1987 | Oelschläger | |
| 4,999,980 | A | | 3/1991 | McGowan | |
| 5,131,490 | A | * | 7/1992 | Bell | 182/7 |
| 5,145,027 | A | | 9/1992 | Petzl et al. | |
| 5,329,884 | A | * | 7/1994 | Bell | 119/857 |
| 5,360,082 | A | * | 11/1994 | Bell | 182/3 |
| 5,433,289 | A | * | 7/1995 | O'Rourke | 182/3 |
| 5,435,272 | A | * | 7/1995 | Epstein | 119/770 |
| 5,445,114 | A | | 8/1995 | Walker | |
| 5,531,292 | A | * | 7/1996 | Bell | 182/3 |
| 5,615,750 | A | | 4/1997 | Phillips | |
| 5,857,540 | A | | 1/1999 | Sadeck | |
| 5,893,367 | A | * | 4/1999 | Dubats et al. | 128/875 |
| 6,039,677 | A | * | 3/2000 | Spletzer | 482/105 |
| 6,050,364 | A | | 4/2000 | Popall et al. | |
| 6,189,651 | B1 | | 2/2001 | Sadeck | |
| 6,244,379 | B1 | | 6/2001 | Larson | |
| 6,253,874 | B1 | | 7/2001 | Casebolt et al. | |
| 6,283,248 | B1 | | 9/2001 | Groover | |
| 6,308,335 | B1 | | 10/2001 | Colorado | |
| 6,367,582 | B1 | * | 4/2002 | Derby | 182/3 |
| 6,374,946 | B1 | | 4/2002 | Petzl et al. | |
| 6,397,389 | B1 | * | 6/2002 | Schultz | 2/69 |
| 6,431,313 | B1 | * | 8/2002 | Petzl et al. | 182/6 |
| 6,438,756 | B1 | * | 8/2002 | Colorado | 2/81 |
| 6,874,596 | B2 | * | 4/2005 | Zeissler et al. | 182/3 |
| 6,942,630 | B2 | * | 9/2005 | Behan | 602/19 |
| 6,971,476 | B2 | * | 12/2005 | Wolner et al. | 182/3 |
| 7,066,181 | B2 | * | 6/2006 | West | 128/875 |
| 2003/0062218 | A1 | * | 4/2003 | Zeissler et al. | 182/3 |
| 2005/0067221 | A1 | * | 3/2005 | Wolner et al. | 182/3 |

FOREIGN PATENT DOCUMENTS

| | | | |
|---|---|---|---|
| EP | 0736310 | A2 | 10/1996 |
| FR | 2649618 | A1 | 1/1991 |

OTHER PUBLICATIONS

UIAA Standard UIAA 105 "Mountaineering and Climbing Equipment" (Jan. 2004).

Sked® The "Only" Complete Rescue System, web catalog pages, www.skedco.com/harness.

EVAC Systems Fire and Rescue Equipement, Inc., web catalog pages, www.evacsystems.com.

* cited by examiner

FALL PROTECTION HARNESS

This application claims priority based on U.S. provisional application No. 60/527,992 filed on Dec. 9, 2003, which is incorporated herein by reference in its entirety.

BACKGROUND OF THE INVENTION

The present invention relates to a fall protection harness, and more particularly a fall protection harness which supports various portions of a wearer's body.

Individuals engaged in rigorous activities such as climbing, rescue activities, or construction typically employ equipment or systems to prevent accidental falls. One such system commonly used is a fall protection harness worn by the individual. The harness is typically connected to a rope which is then secured to a structure in a manner well known in the art. Since fall protection harnesses are worn during strenuous physical activities, it is important that the harness not unduly restrict a user's motion.

A sit harness is one common type of fall protection harness. Sit harnesses typically include a belt worn around a user's waist and leg loops which encircle the user's upper legs. The leg loops are typically attached at the front and back to the front and back of the belt by webbing. For some harnesses, the back of the leg loops are often unattached. It is known to provide thin members between the back of the leg loops and the back of the belt. Such members are provided to position the leg loops on the proper portion of the wearer's legs and are not relied upon to support the wearer's weight. Accordingly, sit harness of the prior art only support a wearer at the waist and thighs. No support is provided for the wearer's buttocks. This can lead to discomfort especially in situations where a wearer is relying on the harness to support his or her weight for extended periods of time, such as during rock climbing.

Sit harnesses of the prior art which use thin webbing to attach the leg loops to the belt are prone to tangling during nonuse, as the straps and leg loops become intertwined. This is especially the case when more than one harness is stored together. The straps supporting the leg loops are typically removable from the belt or leg loops, therefore, in addition to untangling the harness, a wearer may have to reassemble straps that have come loose before putting on the harness. These types of harnesses are also typically difficult to put on since the leg loops, which are held to the belt by only thin straps, have to be properly held in positioned when the legs are inserted.

Accordingly, it is desirable to provide a fall protection harness, which provides support over a significant portion of a user's body without restricting movement. It is also desirable to provide a fall protection harness that is easy to put on and comfortable to wear when suspending the wearer or when the user is in an unsuspended position.

SUMMARY OF THE INVENTION

It is an advantage of the present invention to provide a fall protection harness having a waist belt and weight supporting loops secured to the belt at the front and back.

It is an advantage of the present invention to provide a fall protection harness having a support material extending from the belt portion to the weight supporting loops.

It is a further advantage of the present invention to provide a harness that creates a one piece, form fitting, high strength harness that distributes the weight of the person wearing the harness across portions of the wearer's lower waist, buttocks and legs while allowing maximum flexibility and comfort.

For the purposes of the present invention, the terms "wearer" and "user" are used interchangeably.

The present invention is a fall protection harness that includes: an adjustable belt adapted to be secured around a wearer's waist, wherein the belt has a front, a back, a first side and a second side; a tie-in point on the belt, preferably on the front of the belt, wherein the tie-in point is used to support the wearer; a first weight supporting loop comprising a first front section and a first back section, wherein the first loop is connected to the front of the belt by the first front section and to the back of the belt by the first back section, and wherein the first back section has a first width; a second weight supporting loop comprising a second front section and a second back section, wherein the second loop is connected to the front of the belt by the second front section and to the back of the belt by the second back section, and wherein the second back section has a second width; a first lateral member extending between the first front section and the first back section; and a second lateral member extending between the second front section and the second back section. The first weight supporting loop and the first lateral member and the second weight supporting-loop and the second lateral member define openings that are adapted to encircle a wearer's legs, and the back sections of the weight supporting loops are adapted to support the wearer's lower back and/or buttocks.

In another embodiment of the fall protection harness, the first front section is connected to the second front section instead of connecting to the front of the belt. A connecting device, preferably a ring, most preferably a metal ring, is used to connect the first and the second front sections to the front of the belt.

In a preferred embodiment of the fall protection harness, each of the back sections has a maximum width of at least 3 inches. In another embodiment each of the first and the second widths of the back sections is a minimum of 2 inches between the lateral members and the back of the belt. Preferably, the widths decrease as the back sections extend downwardly, from the back of the belt to a point above where the back sections are joined to the lateral members, and wherein each of the widths increases after that point. In a preferred embodiment, the first width tapers inwardly from the first side as it extends downwardly from the belt and the second width tapers inwardly from the second side as it extends downwardly from the belt.

In another preferred embodiment of the harness, the first and the second lateral members are adjustable and adapted to be secured around the outside of the wearer's legs. The first and the second weight supporting loops are adopted to encircle the wearer's buttocks and crotch. The belt, weight supporting loops and lateral members are all formed of the same continuous weight bearing material. Preferably, the material comprises at least two layers, a first continuous layer and a second discontinuous layer. In a most preferred embodiment, the belt and the weight supporting loops are integrally formed as one continuous structure.

In a most preferred embodiment of the fall protection harness, the first front section is attached to the front of the belt at a first position and the second front section is attached to the front of the belt at a second position, which is laterally offset along the belt from the first position.

In another embodiment of the fall protection harness, the front of the belt has a first dimension measured downwardly from the top of the belt and the back of the belt has a second dimension measured downwardly from the top of the belt, which is at least twice the first dimension.

One embodiment of the of the fall protection harness includes a pair of shoulder straps, wherein each shoulder strap is secured to the front and back of the belt and adapted to extend upwardly over a user's shoulders. Each shoulder strap comprises a front section and a back section adapted to extend over the user's chest and back, respectively. Preferably, the shoulder straps are adjustable to allow the harness to snugly fit users of various heights and weights. In some embodiments, the harness includes at least one chest strap, preferably adjustable, which extends between the front sections of the shoulder straps and at least one lateral back support which extends between the back sections of the shoulder straps. The shoulder straps, chest straps and lateral back supports are preferably formed from the same continuous weight bearing material as the belt, weight supporting loops and lateral members.

DETAILED DESCRIPTION OF THE PREFERRED EMBODIMENTS

The present invention is directed to a harness which may be worn by an individual during such activities as climbing, mountaineering, caving, rescue and industrial work. The harness is connectable to a support line such as a climbing rope and provides a degree of protection against falls which may occur during such activities. The harness of the present invention may be in the form of a sit harness which is secured about a wearer's waist and thighs. In an alternative embodiment, the harness of the present invention may be in the form of a full body harness secured about a wearer's waist, thighs and torso. The harness preferably includes a one-piece, form-fitting, high-strength seat that distributes the forces across the entire surface area of the user's lower body while allowing maximum flexibility and comfort.

Figure 1:
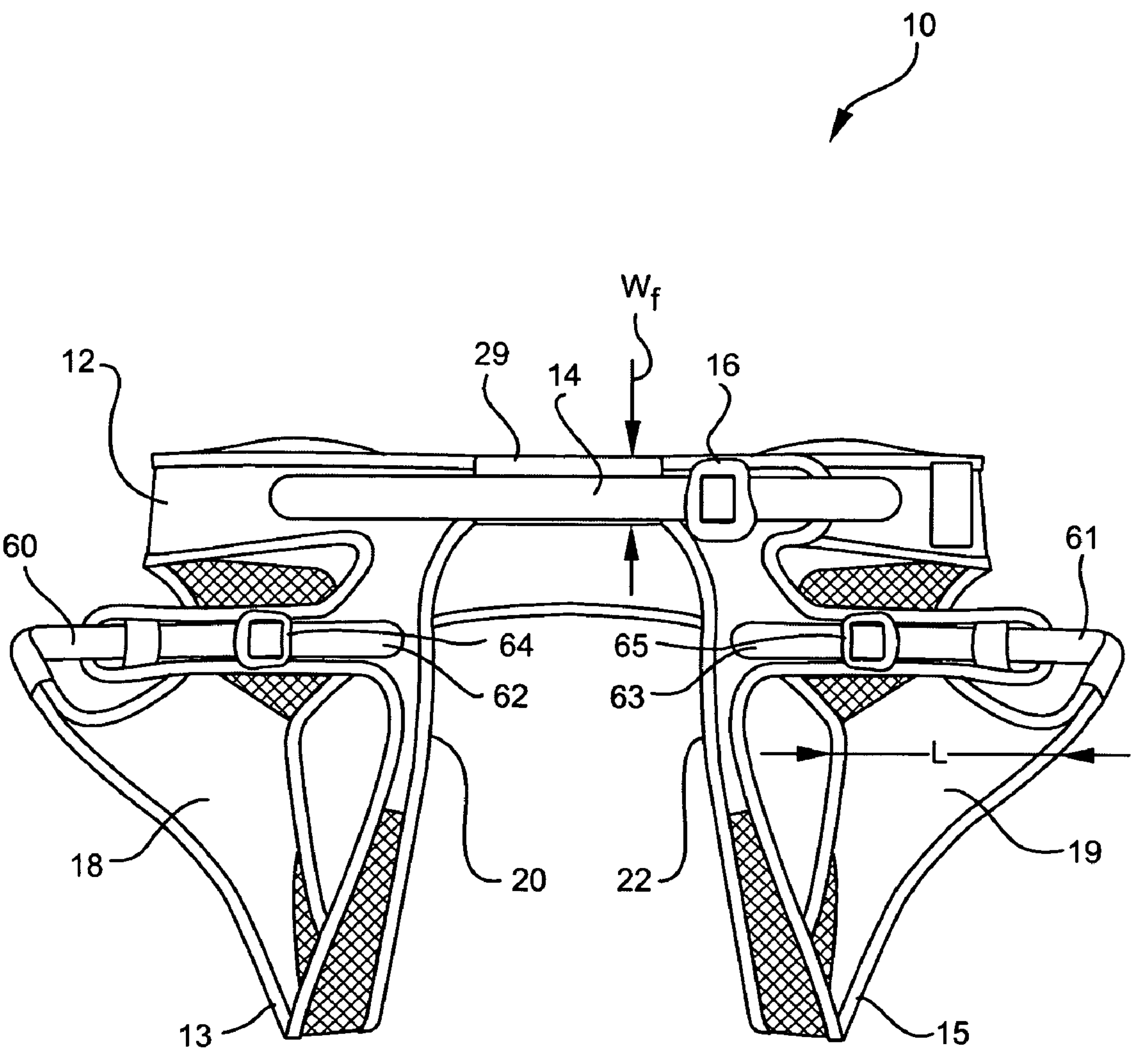
FIG. 1 is a front elevational view of a preferred embodiment of the harness of the present invention.
Figure 2:
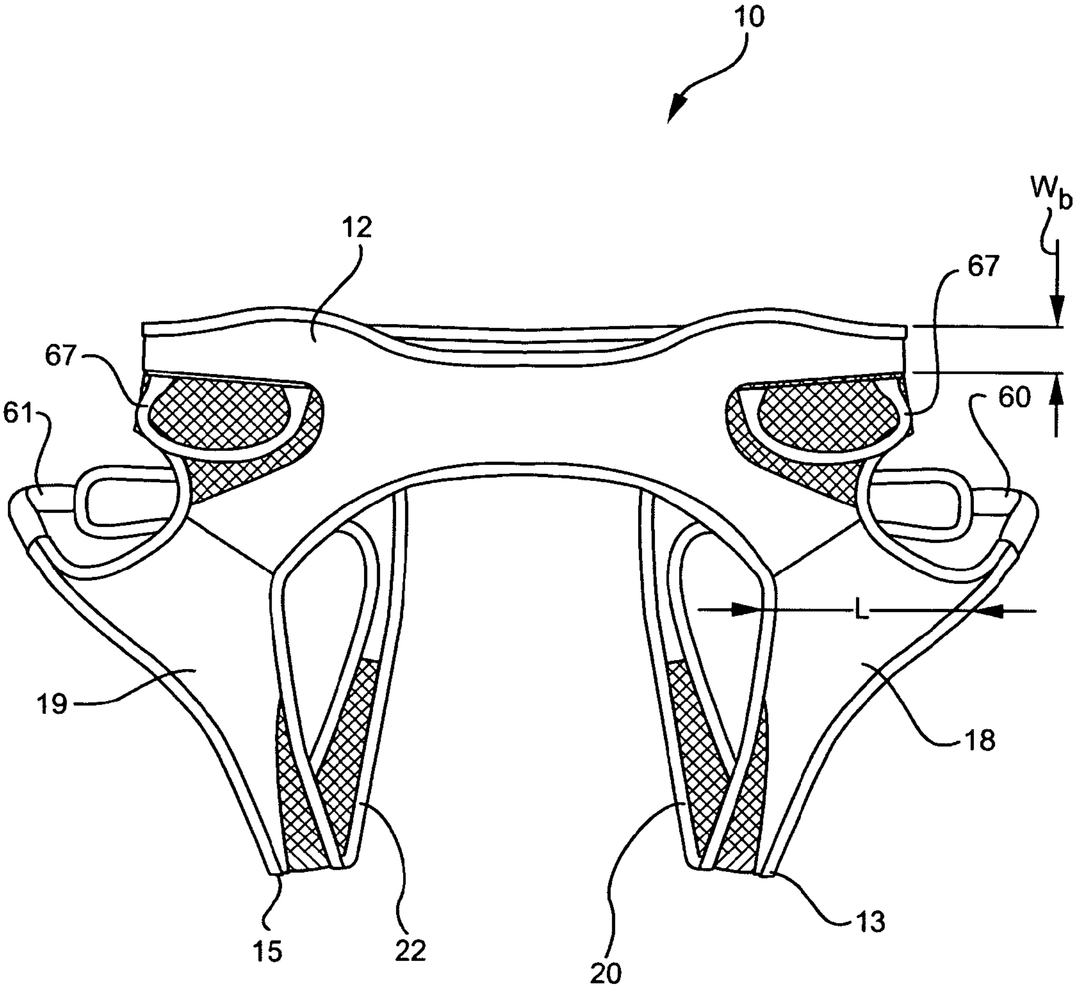
FIG. 2 is a back elevational view of the harness of FIG. 1.
Figure 3:
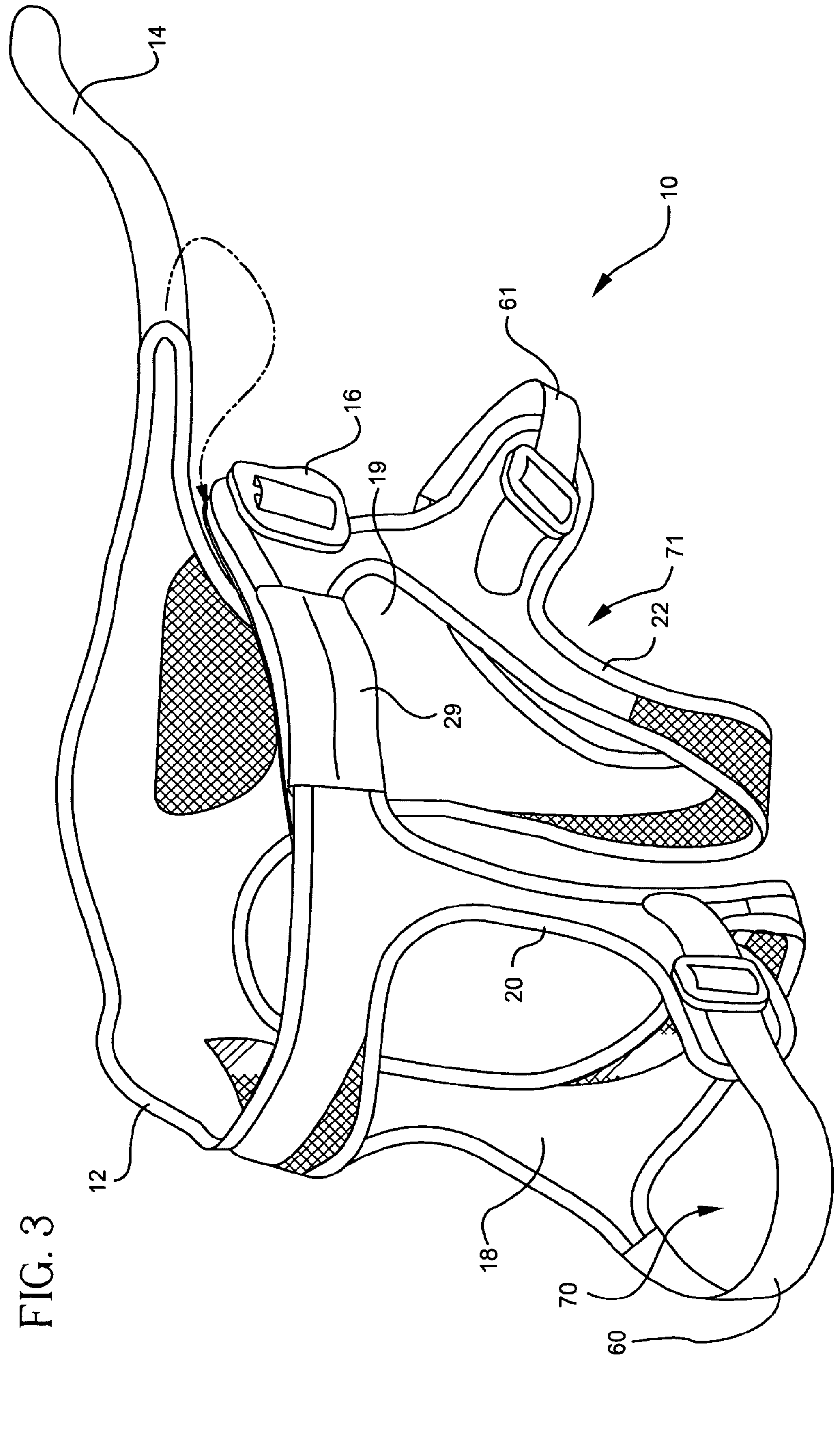
FIG. 3 is a perspective view of the harness of FIG. 1 with the belt strap unsecured.

FIGS. 1-3 show a preferred embodiment of the harness 10 that includes an upper portion which forms an adjustable waist belt 12 that is adapted to encircle a wearer's waist. The harness 10 is designed to be worn over clothing. The belt 12 has two ends which are connected to each other in order to secure the belt 12 around the wearer. One end of the belt 12 may include flexible members forming a strap 14 and the other end may include an attachment device 16, such as a D-ring, buckle or clasp. Strap 14 is connected to the attachment device 16 in order to provide the wearer with a secure fit. In a preferred embodiment, the attachment device 16 uses a D-ring to form at least one self jamming loop.

Depending downwardly from belt 12 are a pair weight supporting loops 13 and 15 which include back sections 18 and 19. The upper portions of back sections 18 and 19, that is the portions from the belt to the points where the lateral members 60 and 61 are connected, have a maximum lateral width, L, of at least 2 inches, and preferably at least 3 inches, in order to provide support for the user's buttocks and upper legs. For the purposes of the present invention, the term lateral width, L, as used to describe the back sections 18 and 19 and as shown in FIGS. 1 and 2, refers to the distance from one side of the back section 18 or 19 to the opposing side as it extends downwardly from the belt 12. The weight supporting loops 13 and 15 also include front sections 20 and 22 which extend downwardly from the front of the belt 12 and join the back sections 18 and 19 to form the weight supporting loops 13 and 15.

In a preferred embodiment, each of the back sections 18 and 19 tapers inwardly from the center of the back of the belt 12 and the respective sides for a short distance as it extends downwardly. The back sections 18 and 19 then widen to provide support for the wearer's buttocks and subsequently narrow to allow the weight supporting loops 13 and 15 to extend between the wearer's legs. This configuration of the back sections 18 and 19 provides ventilation and comfort while minimizing the weight of the harness 10.

Each of the weight supporting loops 13 and 15 also includes a pair of lateral members 60 and 61 which extend between the back sections 18 and 19 and the front sections 20 and 22 and are adapted to fit around the outside of the wearer's legs. The lateral members 60 and 61 and the lower portions of the weight supporting loops 13 and 15 form openings 70 and 71 (see FIG. 3) through which the wearer's legs extend. In a preferred embodiment, the lateral members 60 and 61 are adjustable in order to securely position the harness 10 around the wearer. In a most preferred embodiment, each of the lateral members 60 and 61 comprises a fastening member 62 and 63 and a securing member 64 and 65. The fastening members 62 and 63 are preferably straps which adjustably engage the securing members 64 and 65, preferably D-rings so that the lateral members 60 and 61 snugly fit around the wearer's legs.

As shown in FIGS. 1 and 2, the pair of weight supporting loops 13 and 15 each form a continuous structure that attaches to the front and back of the belt 12 to provide support for the wearer. Both the front sections 20 and 22 and the back sections 18 and 19 extend downwardly from the front and back of the belt 12, respectively, and are joined together at their lower ends. In the preferred embodiments of the invention, each of the weight supporting loops 13 and 15 is a continuous structure that includes the front sections 20 and 22 and the back sections 18 and 19. The back sections 18 and 19 are wider near their midpoint than at the top and bottom in order to provide maximum support for the wearer while also providing freedom of movement.

FIG. 2 shows how the back sections 18 and 19 are designed to conform to the wearer's lower back and buttocks. The sides of the harness 10 are open below the belt 12 to allow the wearer's hips unrestricted movement. Each of the back sections 18 and 19 tapers inwardly from the side and the middle of the belt 12 and then flares outwardly to a maximum width at a point which coincides with the wearer's buttocks in order to distribute the wearer's weight across a larger area when the wearer is suspended by the belt 12. As the back sections 18 and 19 extend downwardly below this point, their widths decrease so that the weight supporting loops 13 and 15 can pass between the wearer's legs. The narrow width of the weight supporting loops 13 and 15 at the point where they pass between the wearer's legs provides comfort and maximum freedom of movement for the wearer.

FIG. 2 also shows handles 67 on the back of the belt 12. These handles 67 can be located anywhere on the belt 12 and they provide attachment points for securing climbing gear and other equipment that the wearer may choose to carry. These handles 67 can also be grasped by other persons and used to either assist or lift the wearer.

In a preferred embodiment, the width of the back of the belt 12 is greater than the width of the front. For the purposes of this invention, the width of the belt 12 is defined as the dimension from the top of the belt extending downwardly when the belt 12 is positioned around the waist of the wearer. This provides increased support for the wearer's lower back, but does not restrict the wearer's ability to bend forward. In a most preferred embodiment, the back of the belt 12 has a minimum width, $W_b$, of 3 inches (as shown in FIG. 2). In another embodiment, the width, $W_b$, of the back of the belt is at least twice the width, $W_f$, of the front of the belt 12 (as shown in FIG. 1).

The fall protection harness 10 also includes at least one securement loop 29 permanently attached to the belt 12 and used to attach a rope or cable to the harness 10. Preferably, a securement loop 29 is located at the front of the belt 12 so that when the wearer is suspended by a rope, he or she can easily hold on to the rope and control his or her movement. The securement loop 29 is made of a high strength material similar to the material used for the harness 10 and stitched to the belt 12. The securement loop 29 can also be made from metal and can be attached to the belt 12 with rivets or other fastening hardware well known to those skilled in the art. In one embodiment, the securement loop 29 is a metal loop, preferably stainless steel, which is not attached to the belt 12, but instead encircles the belt 12 between the two front sections 20 and 22.

FIG. 3 also shows the preferred embodiment of the fall protection harness 10, wherein the belt strap 14 can be removed from the attachment device 16, preferably a D-ring, to allow the wearer to easily place his or legs into the openings 70 and 71 in the harness 10.

Figure 4:
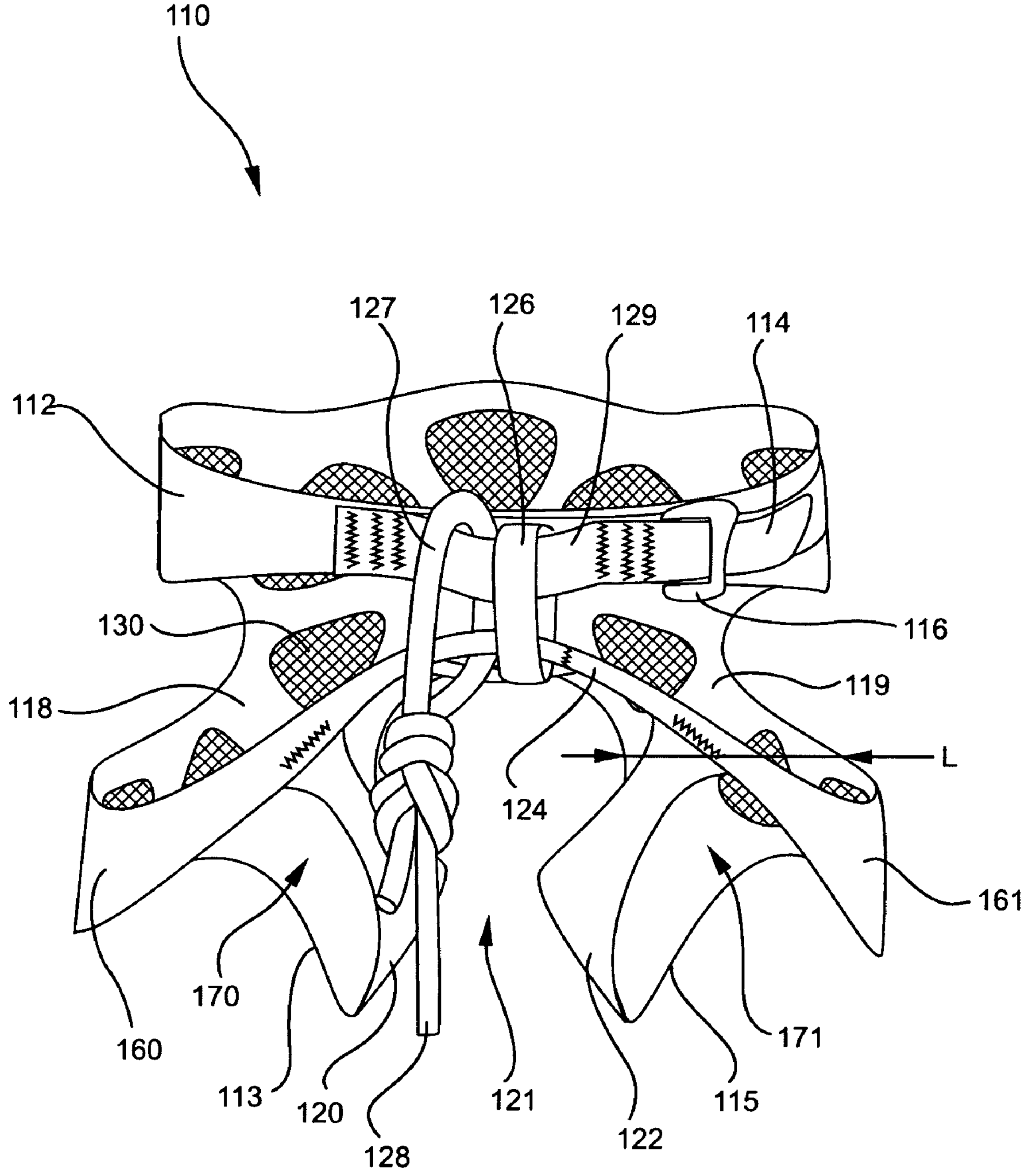
FIG. 4 is a front elevational view of an alternative embodiment of the harness of the present invention.
Figure 5:
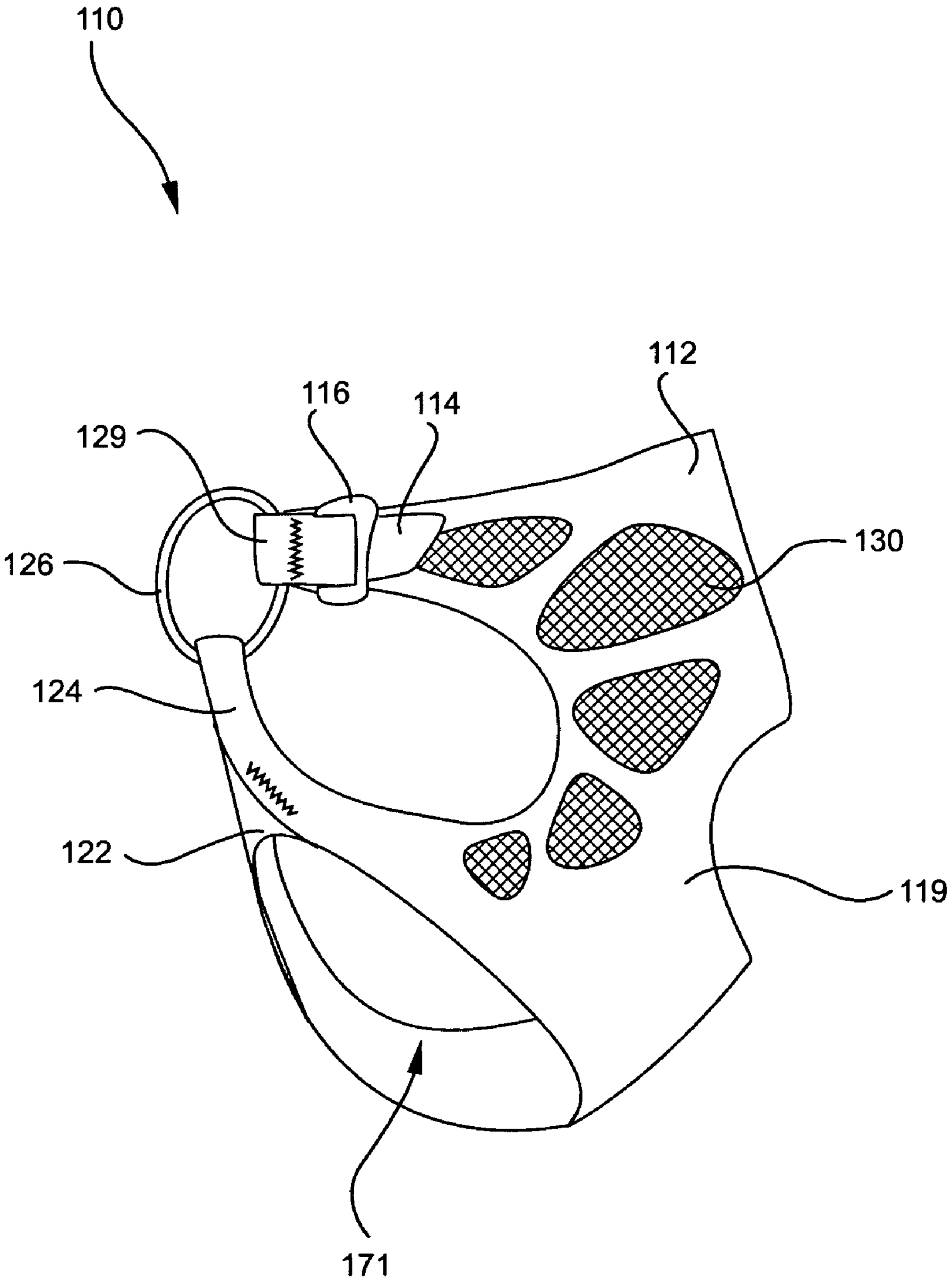
FIG. 5 is a side elevational view of the harness of FIG. 4.

FIGS. 4 and 5 show another embodiment of the harness 110 which includes an upper portion forming a waist belt 112 that is positionable about a user's waist. One end of the belt 112 includes a flexible member, preferably a strap 114, and the other end includes an attachment device 116, such as a D-ring, buckle or clasp. Strap 114 engages the attachment device 116 using at least one self jamming loop in order to provide a secure fit.

Back sections 118 and 119 extend downwardly from belt 112 and have lateral widths, L, which provide support for the user's buttocks and upper legs. Back sections 118 and 119 are joined to front sections 120 and 122, respectively, to form weight supporting loops 113 and 115. Lateral members 160 and 161 extend from the back sections 118 and 119 and attach to the front sections 120 and 122. The weight supporting loops 113 and 115 and the lateral members 160 and 161 form openings 170 and 171 through which a user's legs are inserted. In a preferred embodiment, weight supporting loops 113 and 115 are formed from a continuous material that includes the back sections 118 and 119 together with front sections 120 and 122. After the front sections 120 and 122 are attached to the lateral members 160 and 161, they attach to each other by a connecting portion 124. The connecting portion 124 extends upwardly and is secured to belt 112 by a ring 126, thereby securing the front sections 120 and 122 to the belt 112. The connecting portion 124 supports the front sections 120 and 122 and makes it easier for a wearer to get into the harness.

The front of belt 112 preferably includes a tie-in point 127 where the rope 128 or other securement line may be attached to harness 110. The tie-in point 127 includes a securement loop 129 formed by sewing or fastening the ends of a piece of high strength fabric to one of the straps 114 of belt 112. The securement loop 129 can also be a metal ring or half ring attached to the belt 112 with rivets or similar attachment hardware known to those skilled in the art. Securement loop 129 forms an opening through which a rope 128 may be attached as shown in FIG. 4. Securement loop 129 may also support ring 126 through which connecting portion 124 runs. In another embodiment, the harness 110 is attached to a securement line by a metal ring (not shown) which encircles the belt 112, preferably at the front between the weight supporting loops 113 and 115.

The belt 112, front sections 120 and 122, back sections 118 and 119 and lateral members 160 and 161 are all preferably integrally formed to create a fully integrated and unitary harness 110 for supporting the lower portion of a user's body. The user steps into the harness 110 and secures the belt 112 around his or her waist with the attachment device 116. In some embodiments, additional adjustment devices are used to adjust the lateral members 160 and 161 in order to provide a more secure fit.

The harness 110 of the present invention is intended to support the entire weight of a wearer under a fall condition. In case of a fall, a securement line stops the downward movement of the wearer and distributes his or her weight to minimize the resulting shock. Alternatively, a wearer may be suspended from a rope while wearing the harness 110 for extended periods of time such as during rest periods when rock climbing. Harness 110 of the present invention contacts a significant portion of a wearer's body with weight bearing material, and thereby, broadly distributes the weight of the person wearing the harness 110 over those portions of the body resulting in a comfortable and secure device.

Figure 6:
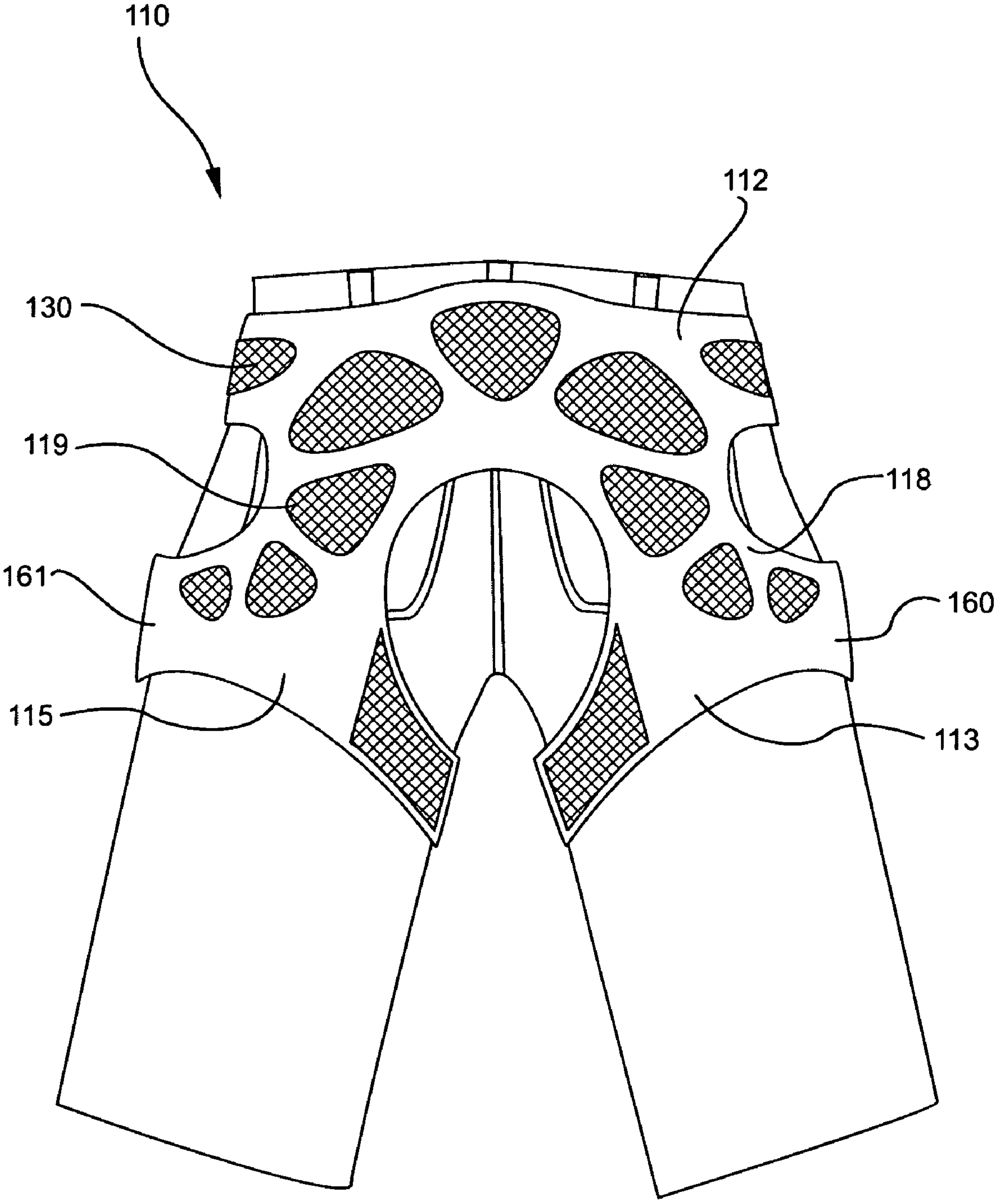
FIG. 6 is a back elevational view of a harness of FIG. 4 showing the harness being worn.
Figure 7:
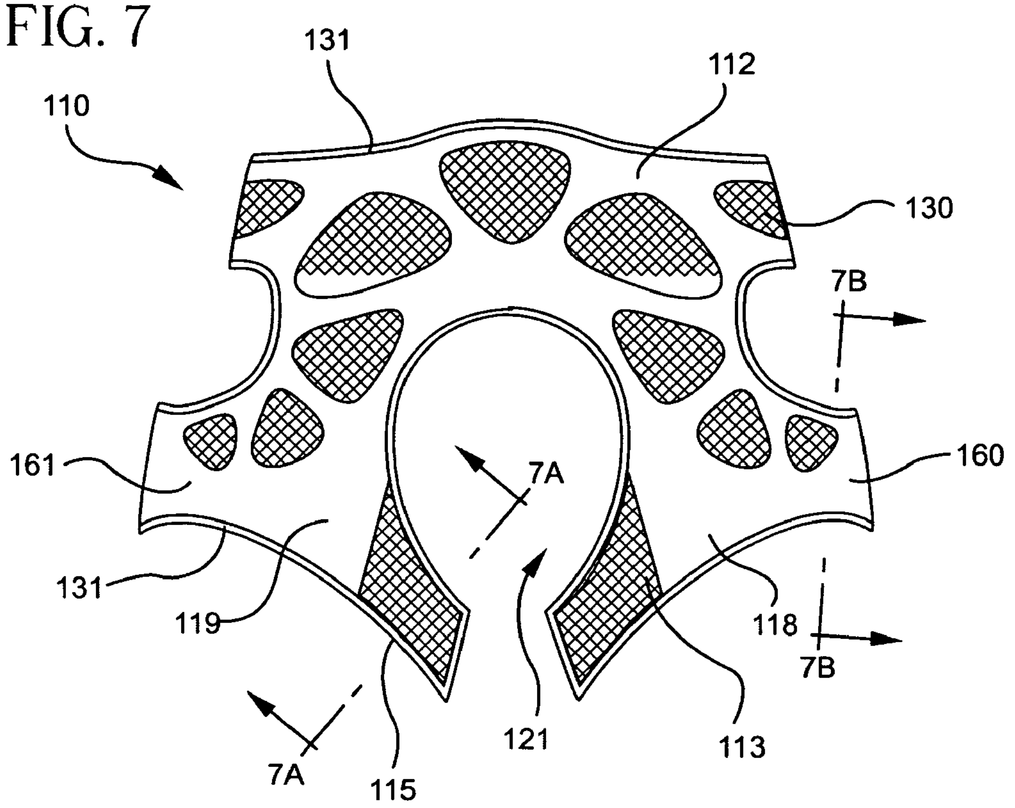
FIG. 7 is a back elevational view of the harness of FIG. 4.
Figure 7A:
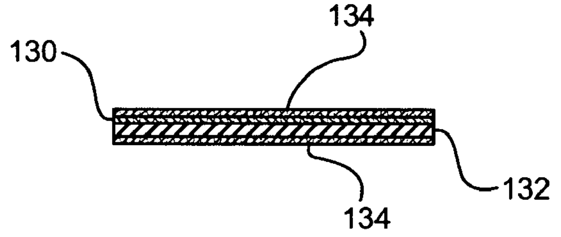
FIG. 7A is an exploded cross-sectional view taken along line A-A of FIG. 7.
Figure 7B:
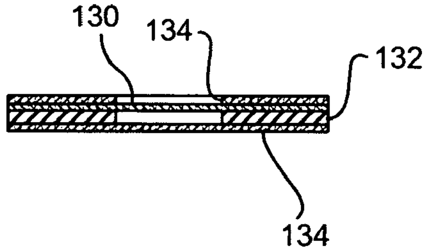
FIG. 7B is an exploded cross-sectional view taken along line B-B of FIG. 7.
Figure 8:
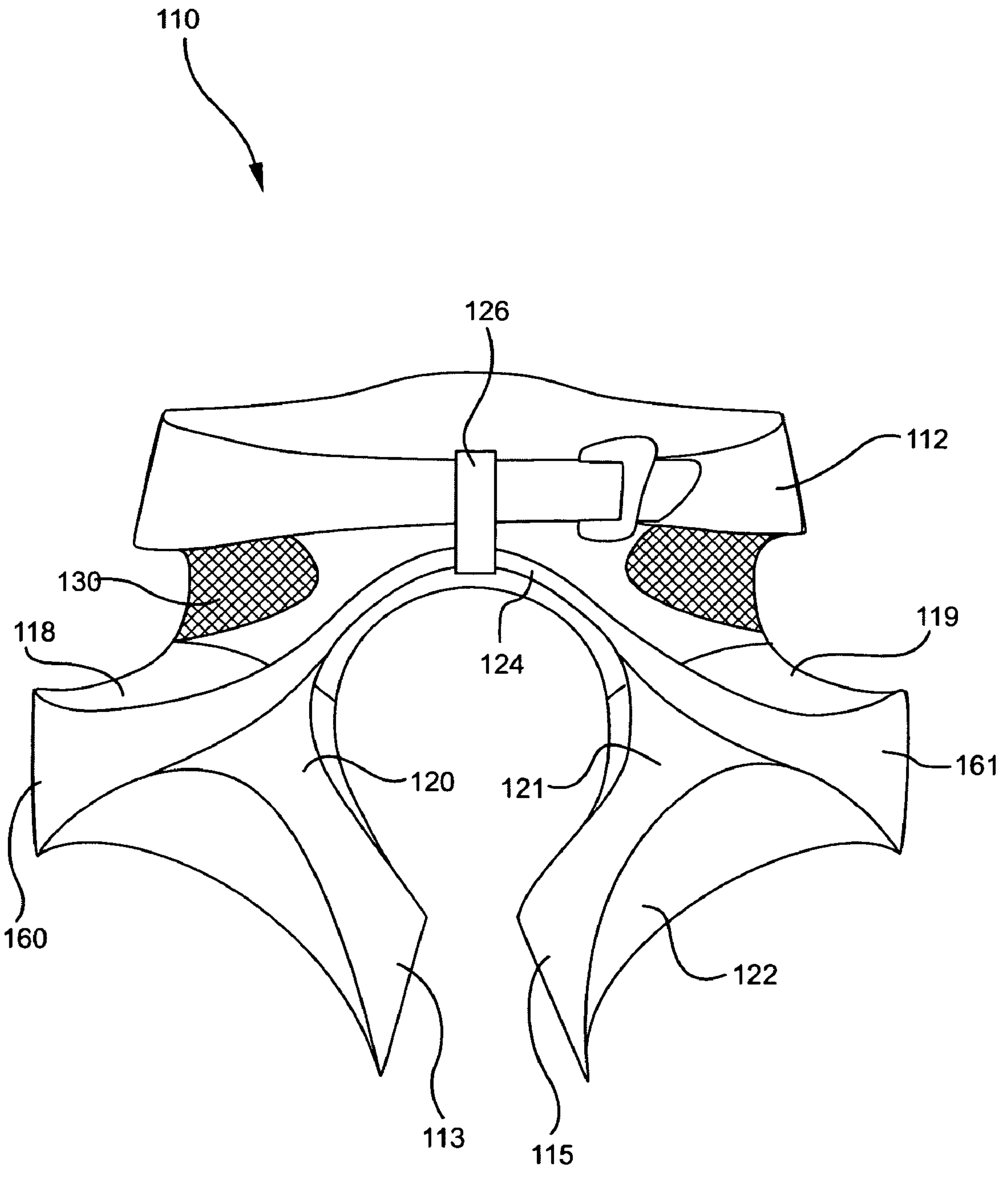
FIG. 8 is a front elevational view of an alternative embodiment of the harness of the present invention.

Referring to FIG. 6, in addition to supporting a wearer at the waist by belt 112, the back sections 118 and 119 provide support in the area of the lower back and buttocks as they extend downwardly from the back of the belt 112 and form two separate structures that are independently connected to the belt. The back sections 118 and 119 narrow slightly in the region of the wearer's hips to provide freedom of movement and then begin to widen as they extend downwardly to the area of the wearer's buttocks. The harness 110 has a significant amount of support material around the buttocks and upper portion of the thighs, which permits the weight of a user suspended by the harness 110 to be distributed over a wide area. FIG. 7 shows that the back of the belt 112 can extend downwardly, preferably at least 2 inches, to provide support for the wearer's lower back. An opening 121 exists between back supports 118 and 119 to allow the wearer to move freely when wearing the harness 110. Since the harness 110 is worn during rigorous activities, the unrestrictive nature of the harness 110 is beneficial to a wearer.

While the dimensions of the various elements can be varied in order to form a safety harness 110 that properly fits the user, the back sections 118 and 119 are preferably not less than three inches wide. This allows the harness 110 to distribute the user's weight across a sufficiently wide area of his or her body so that the harness 110 does not dig into the user and cause injury or discomfort. However, it is within the contemplation of the present invention for the back sections 118 and 119 to be narrower than three inches in some areas, preferably in the lower portions where they pass between the user's legs.

Referring to FIGS. 7, 7A, 7B and 8, the entire harness 110 is preferably constructed of a weight bearing, high-strength material 130 which extends from belt 112 to weight bearing loops 113 and 115. The weight bearing loops 113 and 115 include the back sections 118 and 119 and the front sections 120 and 122, and in some embodiments the connecting portion 124. The preferred high-strength material is a lightweight mesh 130 which is capable of supporting significant loads, such as the weight of a wearer. The mesh 130 is preferably formed of a nylon or a high strength polymer, most preferably Kevlar® reinforced nylon, or other high strength materials used in climbing gear that are well known to those skilled in the art. The sections of the harness 110 formed from mesh 130 are desirable since the mesh 130 provides a light weight material, does not restrict movement, and allows maximum ventilation.

As shown in FIG. 7, a thin piece of boarder material 131, also referred to in the art as binding or ribbing, can be attached to the edges of the mesh 130 in order to secure the perimeter of the mesh 130 and prevent fraying. This border material 131 further enhances the structural integrity of the harness 110 and provides additional support for the wearer.

Figure 9:
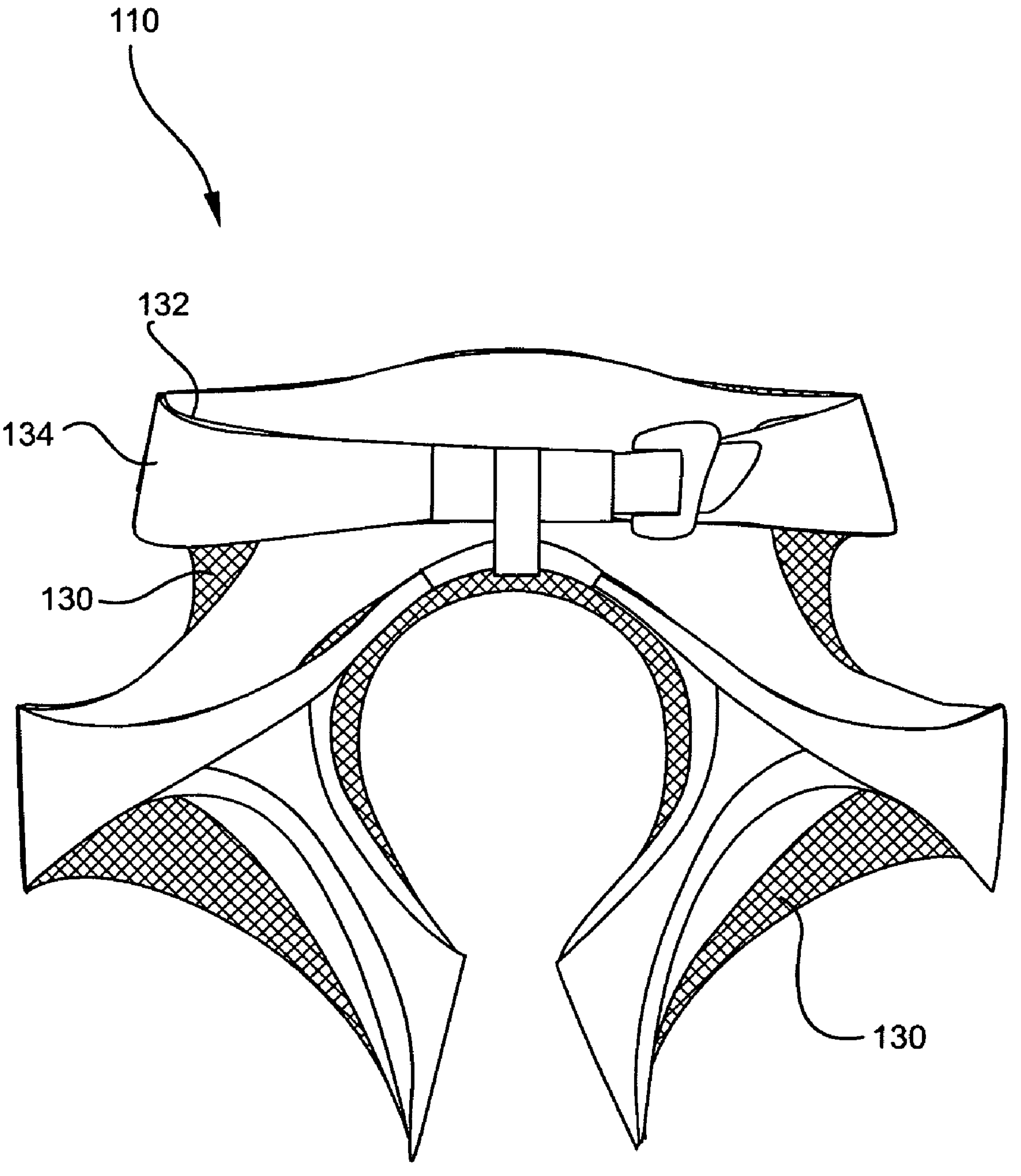
FIG. 9 is a front elevational view of an alternative embodiment of the harness of the present invention showing the location of various materials used to make the harness.

In addition to the high strength material layer 130, other materials may be employed to add additional features to the harness 110. Specifically, various portions of harness 110 may include a layer of padding 132 and/or a layer of covering cloth fabric 134 in order to provide enhanced comfort to a wearer. The padding and covering layers 132 and 134 can be located in strategic areas where such comfort and additional covering is required as shown in FIG. 9. Other areas not requiring padding and covering layers 132 and 134, may simply include the mesh 130 which provides a degree of ventilation to the wearer. In the areas of the harness 110 where the material includes more then one layer, such as layers of mesh 130, padding 132 and fabric 134, the layers are bonded together by a fabric adhesive of a type well known in the art and/or stitched together.

Figure 10:
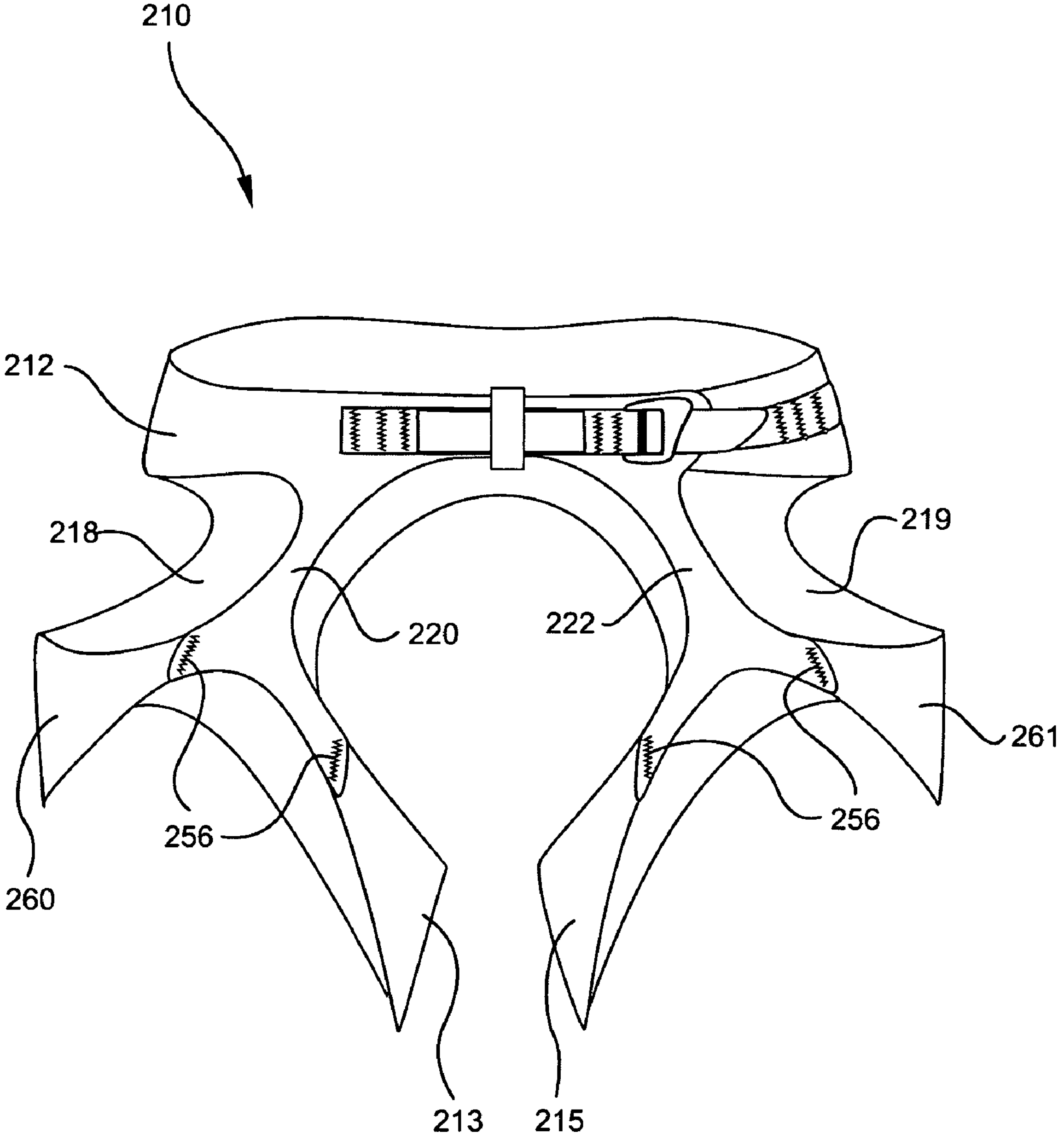
FIG. 10 is a front elevational view of an alternative embodiment of the harness of the present invention.

An alternative embodiment of the present invention is shown in FIG. 10. Harness 210 is formed in a manner similar to that described above, except that the connecting portion 124 shown in FIG. 4 is not used. Instead, the front sections 220 and 222 of the weight supporting loops 213 and 215 are connected directly to the front of the belt 212. Front sections 220 and 222 can be integrated with belt 212 and connected by stitching 256 or other secure fastening means to the lateral members 260 and 261. Front sections 220 and 222 and lateral members 260 and 261 are formed of the same high strength material as the belt 212 and the back sections 218 and 219. Front sections 220 and 222 are preferably narrower than back sections 218 and 219 in order to allow the wearer maximum flexibility and movement.

Figure 11:
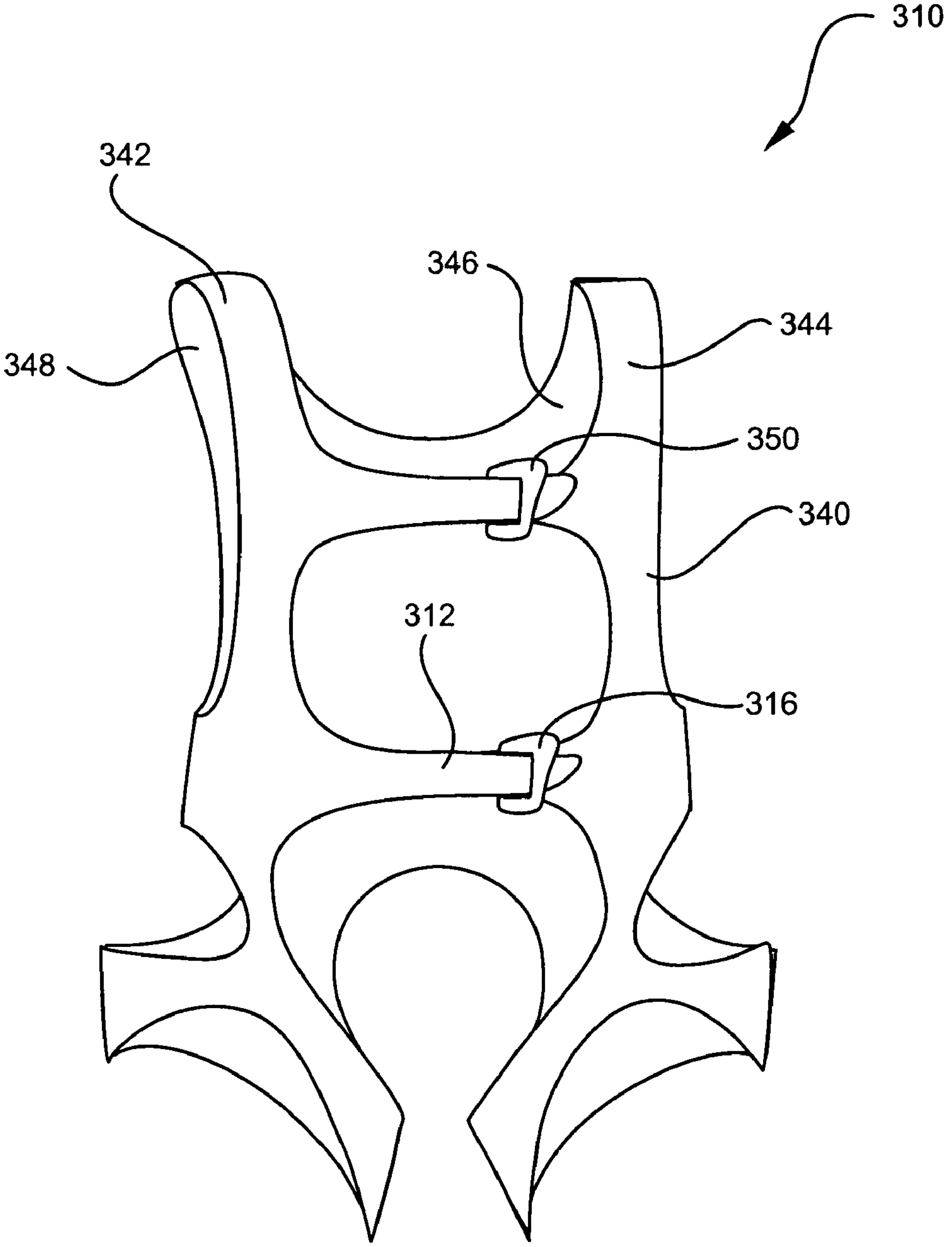
FIG. 11 is a front elevational view of an embodiment of the harness of the present invention which includes shoulder straps.

In another alternative embodiment shown in FIG. 11, the harness 310 of the present invention includes a top portion 340 extending above the belt 312. The top portion 340 includes shoulder straps 342 and 344, which are adapted to extend over the shoulders of a user. In a preferred embodiment, at least one chest strap 348, which can be adjustable, joins the shoulder straps 342 and 344 at about the midpoint between the belt 312 and the top of the user's shoulders. In another preferred embodiment, the top portion 340 has at least one lateral back support (not shown) which extends between the shoulder straps 342 and 344 across the back of the wearer. Each of the shoulder straps 342 and 344 forms a loop extending upwardly from the front of the belt 312 and then downwardly to the back of the belt 312. The shoulder straps 342 and 344 are securely fastened to the belt 312 and in a preferred embodiment they are integrally formed with the belt 312. In one embodiment, the shoulder straps 342 and 344 are adjustable and each strap includes two members which are securely joined together with a connecting device (not shown), preferably a D-ring. This allows the shoulder straps 342 and 344 to securely fit over the wearer's shoulders and provide maximum support.

In one embodiment, the top portion 340 of the harness 310 has a vest-like construction with openings 346 and 348 for the wearer's head and arms, respectively. In addition to the belt attachment device 316, a preferred embodiment has a second attachment device 350 which is located across the chest of a wearer. The top portion 340 of the harness 310 is formed of the same load bearing mesh which forms the harness in the previously described embodiments. Various portions of the shoulder straps 342 and 344 can also include padding and/or fabric attached to the mesh in order to provide increased comfort.

Thus, while there have been described the preferred embodiments of the present invention, those skilled in the art will realize that other embodiments can be made without departing from the spirit of the invention, and it is intended to include all such further modifications and changes as come within the true scope of the claims set forth herein.

I claim:

1. A fall protection harness comprising:

an adjustable belt adapted to be secured around a wearer's waist, wherein said belt has a front and a back;

a tie-in point on said belt, wherein said tie-in point is used to support the wearer;

a first weight supporting loop comprising a first front section and a first back section, wherein said first loop is connected to the front of said belt by said first front section and to the back of said belt by said first back section;

a second weight supporting loop comprising a second front section and a second back section, wherein said second loop is connected to the front of said belt by said second front section and to the back of said belt by said second back section;

a first lateral member extending between said first front section and said first back section; and a second lateral member extending between said second front section and said second back section;

wherein said first and said second weight supporting loops are adopted to encircle the wearer's buttocks and crotch and said lateral members are adapted to be secured around the outside of said wearer's legs, and wherein said first back section has a first width and said second back section has a second width, and wherein said widths decrease as said first and second back sections extend downwardly from the back of said belt to a point above where said first and second back sections are joined to said first and second lateral members, and wherein each of said widths increases after said point.

2. The fall protection harness of claim 1, wherein each of said first and second back sections has a maximum width of at least 3 inches.

3. The fall protection harness of claim 1, wherein each of said first and said second widths is a minimum of 2 inches between the lateral members and the back of the belt.

4. The fall protection harness of claim 1, wherein said first and said second lateral members are adjustable.

5. The fall protection harness of claim 1, wherein the belt, weight supporting loops and said first and second lateral members are all formed of the same continuous weight bearing material.

6. The fall protection harness of claim 1, wherein the first front section is attached to the front of the belt at a first position and the second front section is attached to the front of the belt at a second position, and wherein the first position is laterally offset along the belt from the second position.

7. The fall protection harness of claim 1, wherein the front of the belt has a first dimension measured downwardly from the top of the belt and the back of the belt has a second dimension measured downwardly from the top of the belt, and wherein said second dimension is at least twice the first dimension.

8. The fall protection harness of claim 1, wherein the harness includes a first layer and a second layer, said first layer is continuous and said second layer is discontinuous.

* * * * *